United States Patent
Lee et al.

(10) Patent No.: US 10,278,903 B2
(45) Date of Patent: May 7, 2019

(54) COMPOSITE POWDER HAVING INORGANIC POWDER IMPREGNATED WITH POROUS POLYMER, COSMETIC COMPOSITION CONTAINING SAME, AND METHOD FOR PREPARING SAME

(71) Applicant: AMOREPACIFIC CORPORATION, Seoul (KR)

(72) Inventors: Hyun Suk Lee, Yongin-si (KR); Yong Jin Kim, Yongin-si (KR); Jon Hwan Lee, Yongin-si (KR); Se Jun Park, Yongin-si (KR); Kyung Ho Choi, Yongin-si (KR); Yeong Jin Choi, Yongin-si (KR); Sung-Wook Choi, Bucheon-si (KR); Dong-Hyun Paik, Siheung-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/555,863

(22) PCT Filed: Nov. 24, 2015

(86) PCT No.: PCT/KR2015/012663
§ 371 (c)(1),
(2) Date: Sep. 5, 2017

(87) PCT Pub. No.: WO2016/148375
PCT Pub. Date: Sep. 22, 2016

(65) Prior Publication Data
US 2018/0042823 A1  Feb. 15, 2018

(30) Foreign Application Priority Data
Mar. 13, 2015 (KR) .................. 10-2015-0035097
Jul. 20, 2015 (KR) .................. 10-2015-0102194

(51) Int. Cl.
*A61K 8/29* (2006.01)
*A61K 8/02* (2006.01)
(Continued)

(52) U.S. Cl.
CPC ............ *A61K 8/022* (2013.01); *A61K 8/0279* (2013.01); *A61K 8/19* (2013.01); *A61K 8/26* (2013.01);
(Continued)

(58) Field of Classification Search
CPC ........ A61K 8/022; A61K 8/29; A61K 8/8147; A61Q 1/02; C08J 2333/02; C08J 3/122
See application file for complete search history.

(56) References Cited

U.S. PATENT DOCUMENTS 5,306,486 A * 4/1994 McCook .................. A61K 8/29
424/59
7,247,378 B2 7/2007 Kim et al.
(Continued)

FOREIGN PATENT DOCUMENTS

EP  1964875 A1  9/2008
EP  2229931 A1  9/2010
(Continued)

OTHER PUBLICATIONS

Kang et al. (EP1291370B1; English translation; May 2009; 15 pages). (Year: 2009).*
(Continued)

*Primary Examiner* — Ernst V Arnold
(74) *Attorney, Agent, or Firm* — Lucas & Mercanti, LLP (57) ABSTRACT

The present invention relates to composite powder having enhanced water repellency and oil absorbency by means of even impregnation of inorganic powder particles with a super-water-repellent porous polymer. The composite powder prepared by means of a one-step spraying procedure of
(Continued)

electro-spraying or spray drying, according to the present invention, shows super water repellency and maximized oil absorbency by means of increased porosity of porous polymethyl methacrylate (PMMA) and even impregnation with titanium dioxide ($TiO_2$) nanoparticles.

6 Claims, 7 Drawing Sheets

(51) Int. Cl.
    *A61K 8/27*         (2006.01)
    *A61K 8/19*         (2006.01)
    *A61K 8/81*         (2006.01)
    *A61Q 1/02*         (2006.01)
    *C08J 3/12*          (2006.01)
    *A61K 8/26*         (2006.01)
    *A61Q 1/00*         (2006.01)
    *A61Q 1/12*         (2006.01)

(52) U.S. Cl.
    CPC ............... *A61K 8/27* (2013.01); *A61K 8/29* (2013.01); *A61K 8/817* (2013.01); *A61K 8/8147* (2013.01); *A61K 8/8152* (2013.01); *A61K 8/8176* (2013.01); *A61Q 1/00* (2013.01); *A61Q 1/02* (2013.01); *A61Q 1/12* (2013.01); *C08J 3/122* (2013.01); *A61K 2800/654* (2013.01); *C08J 2333/02* (2013.01)

(56) References Cited

U.S. PATENT DOCUMENTS

| | | | | |
|---|---|---|---|---|
| 2002/0143403 | A1* | 10/2002 | Vaidyanathan | ....... A61L 27/446 623/23.51 |
| 2012/0034281 | A1 | 2/2012 | Kaneko et al. | |

FOREIGN PATENT DOCUMENTS

| | | | | |
|---|---|---|---|---|
| EP | 2420221 | A1 | 2/2012 | |
| EP | 2420221 | A1 * | 2/2012 | ............. A61K 8/375 |
| EP | 2810959 | A1 | 12/2014 | |
| JP | 2011201832 | A | 10/2011 | |
| JP | 2012-233148 | A | 11/2012 | |
| JP | 2013028563 | A | 2/2013 | |
| KR | 1019990012219 | A | 2/1999 | |
| KR | 20030020515 | A | 3/2003 | |
| KR | 10-2007-0094166 | A | 9/2007 | |
| KR | 20120098974 | A | 9/2012 | |
| KR | 20130011584 | A | 1/2013 | |
| KR | 101261784 | B1 | 5/2013 | |
| WO | 2010/038065 | A2 | 4/2010 | |
| WO | 2010114125 | A1 | 10/2010 | |
| WO | 2012/105060 | A1 | 8/2012 | |

OTHER PUBLICATIONS

International Search Report for International Application No. PCT/KR2015/012663 (11 Pages) (dated Feb. 29, 2016).
Extended European Search Report, 15885676.5, dated Jan. 2, 2018.

\* cited by examiner

| Oil absorption test | |
|---|---|
| Inorganic powder | Oil absorption rate |
| TIO2 CR50 AS | 0.3 |
| Silnos8M (Silica for skin care) | 1.6 |
| Spherica Micro Bead P1500 (Silica for skin care) | 0.7 |
| Scoria | 0.3 |
| SA-MUD01 (Sinan mud) | 0.4 |
| Sunpmma-coco170 (Porous MMA from Sunjin Chemical Co., Ltd.) | 1.6 |
| Porous PMMA + TIO2 50% | 3.0 |

COMPOSITE POWDER HAVING INORGANIC POWDER IMPREGNATED WITH POROUS POLYMER, COSMETIC COMPOSITION CONTAINING SAME, AND METHOD FOR PREPARING SAME

CROSS-REFERENCE TO RELATED APPLICATIONS

This is a 371 of PCT/KR2015/012663, filed on Nov. 24, 2015 which claims the benefit of Korean Patent Application No. 10-2015-0035097, filed Mar. 13, 2015 and Korean Patent Application No. 10-2015-0102194, filed Jul. 20, 2015 the contents of each of which are incorporated herein by reference.

TECHNICAL FIELD

The present invention relates to a composite powder including a porous polymer and inorganic powder particles, and more particularly, to a composite powder having all improved skin covering power, water repellency and oil absorbency because pores of a porous polymer are maintained intact and an inorganic powder is uniformly dispersed on the porous polymer by dispersing the inorganic powder in a solution in which the porous polymer is dissolved, followed by subjecting the dispersion to a one-step spraying process such as spray drying or electro-spraying to prepare a composite powder having the porous polymer impregnated with the inorganic powder, a cosmetic composition including the same, and a method for preparing the same.

BACKGROUND ART

Makeups play an important role in correction of skin blemishes and emphasis of eyes and lips, making the appearance look beautiful. Among the components mixed in makeup cosmetics, coloring materials are used to conceal stains or marks, allowing the skin to look healthy and be tinted with fascinating tones. The coloring materials used in these cosmetics are divided into organic synthetic coloring agents, natural colors, and inorganic pigments.

The organic synthetic coloring agents are classified into a dye, lake, and an organic pigment. The dye is a compound which is dissolved in water, oil, and alcohol, and contains an azo group and the like as a chromophore group, and the lake is a type of an insoluble metal salt bound to a water-soluble dye. The natural colors are extracted from plants, animals, and microorganisms. In this case, such materials have been used as additive materials in foods for a long time because the materials produce poor colors, compared to the synthetic coloring agents. In recent years, the natural colors have again come into the spotlight as the natural colors are used for medicines requiring the safety.

The inorganic pigments are classified into coloring pigments, white pigments, extender pigments, and pearlescent pigments. The coloring pigments give colors to cosmetics, and the white pigments serves to regulate skin covering power. The extender pigments serve to adjust tones as diluents for coloring pigments and play a great role in senses of feeling in use, such as spreadability, adhesion, etc., of products, and formulation of the products. Also, the pearlescent pigments are pigments that endow colors with pearly luster and have a special optical effect, which are used to give an iris color or a metallic luster.

The extender pigments included in conventional cosmetics include talc, kaolin, silica, talc, sericite, calcium carbonate, magnesium carbonate, a silicic acid anhydride, etc., and serve to adjust the depth of color and control spreadability and feeling of formulations, etc. The white pigments include titanium dioxide, zinc oxide, etc. In general, kaolin, talc, silica, and titanium dioxide are basic components of the cosmetics as powders having white color while maintaining applicability, adhesion and skin covering power.

The powders used in the makeup cosmetics require adhesion, hiding power, applicability, spreadability, moisture absorbency, oil absorbency, and skin friendliness, and may be obtained by mixing or applying two or more powders. For example, the inorganic pigments such as titanium dioxide exhibit excellent adhesion, hiding power, etc., but have poor senses of feeling in use such as applicability, spreadability, etc. To make up for these drawbacks, there are known techniques for preparing cosmetics using good hiding power and difference in optical refractive index by coating titanium dioxide with silica at a predetermined ratio to prepare an inorganic composite powder.

However, the conventional coated inorganic composite powder as described above do not exhibit satisfactory characteristics such as stability, adhesion, a sense of feeling in use, and sustainability at the skin and external conditions when actually applied onto the skin.

To solve these drawbacks, methods of performing water repellency treatment using surface treating agents such as silicon compounds, fluorine compounds, metallic soaps, higher alcohols, fatty acids, metal salts of amino acids, lecithin, and the like have been proposed in the related art. Among theses, a surface treatment method using silicon compounds or metal salts of amino acids is common. In recent years, a surface treatment method using a combination of the two methods has been proposed.

Meanwhile, the coated powder whose surface is treated with a fatty acid, a metallic soap, and a metal salt has good adhesion to the skin and a good sense of feeling in use on the skin, but has poorer water resistance than the powder surface-treated with the silicon compound and exhibits insufficient spreadability due to somewhat a rough sense of feeling when applied onto the skin. Also, because the metal salt is absorbed onto a surface of the powder in the form of fine particles, the metal salt may be detached due to poor stability in a surface-modified state. In addition, the coated powder still has problems regarding degraded color reproduction when used together with other silicon raw materials.

DISCLOSURE

Technical Problem

Makeup cosmetics include a powder having oil absorbency for the purpose of preventing makeup sustainability from being degraded due to the presence of sebum, that is, oil excreted from the skin. For example, a resin powder such as porous silica or spherical porous poly(methyl methacrylate) (PMMA) has been used as the powder having oil absorbency. However, the porous silica has a problem in that the dryness of the skin is inevitable because the porous silica absorbs moisture as well as the skin oil, and the porous poly(methyl methacrylate) has a problem in that it has undesirable absorption performance due to a small pore diameter thereof.

Also, because the inorganic powder among the components of the makeup cosmetics, either the coloring pigment or white pigment serving to regulate the color or hiding power of the skin is included regardless of the porous raw material, the makeup cosmetics has problems in that, as the pigment is directly exposed to the sebum when applied onto the skin, the lumping of cosmetics may be caused, resulting in highly degraded makeup sustainability.

Technical Solution

Therefore, the present invention is designed to solve the problems of the prior art, and it is an object of the present invention to provide a composite powder having a porous polymer impregnated with an inorganic powder, which is prepared by dispersing the inorganic powder in a solution in which the porous polymer is dissolved, followed by subjecting the dispersion to a one-step spraying process such as spray drying or electro-spraying so that the porous polymer is uniformly impregnated with inorganic powder particles.

The porous polymer of the present invention having a sebum absorption ability may include one or more selected from the group consisting of poly(methyl methacrylate) (PMMA), poly(vinyl pyrrolidone) (PVP), poly(caprolactone) (PCL), and poly(L-lactic acid) (PLLA). Preferably, poly(methyl methacrylate) is used.

Also, the inorganic powder of the present invention may include one or more selected from the group consisting of titanium dioxide ($TiO_2$), zinc oxide, sericite, and iron oxide. Preferably, titanium dioxide is used.

Advantageous Effects

First, the composite powder and the makeup cosmetics of the present invention have improved absorption performance, which has been unsatisfactory when a conventional porous polymer powder is applied alone, by uniformly impregnating the porous polymer with inorganic powder nanoparticles to maintain and enhance a pore diameter and porosity of the porous polymer.

Second, because the makeup cosmetics of the present invention contains the composite powder prepared by a spray drying or electro-spraying method in which the use of an emulsifying agent is avoided, the makeup cosmetics exhibit a characteristic of selectively absorbing sebum only while repelling moisture from the skin by solving a problem regarding degraded water repellency caused due to the incomplete removal of conventional emulsifying agents and realizing super water repellency.

Third, as the method for preparing a composite powder according to the present invention, a spray drying or electro-spraying method is easily applicable to control a specific surface area and an average pore diameter of the porous polymer depending on process conditions.

Fourth, because the porous polymer powder with a spherical shape is uniformly impregnated with the inorganic powder having a crystalline structure by means of the spray drying or electro-spraying that is the method for preparing a composite powder according to the present invention, the composite powder has an effect of improving a sense of feeling in use, for example, soft applicability, due to a rolling effect.

BEST MODE

The present invention relates to a composite powder formed so that a porous polymer is uniformly impregnated with inorganic powder, that is, a composite powder having improved water repellency and oil absorbency, the composite powder being prepared into a composite by impregnating the porous polymer, for example, poly(methyl methacrylate) (PMMA), with the inorganic powder, for example, titanium dioxide ($TiO_2$) nanoparticles, a cosmetic composition including the same, and a method for preparing the same.

Among the powders included in the makeup cosmetics, types of titanium dioxide are divided into titanium dioxide for blocking ultraviolet rays and titanium dioxide for covering the skin. In this case, the titanium dioxide used for blocking ultraviolet (UV) rays has a relatively small average particle size of 10 to 200 nm to have a UV-ray blocking effect. Meanwhile, the titanium dioxide for covering the skin has an average particle size of 200 to 350 nm and has almost no UV-ray blocking effect, but is used for a pigment for scattering visible light and covering stains, freckles, red spots, blemishes, and the like of the skin due to its excellent hiding power.

The present invention relates to conventional titanium dioxide for covering the skin among the aforementioned types of titanium dioxide. Accordingly, there is provided a composite powder in which poly(methyl methacrylate), which is the porous polymer having an oil absorption ability with respect to sebum, is impregnated with titanium dioxide nanoparticles having a diameter of 200 to 300 nm.

The present invention is also applicable to the composite powder in which poly(methyl methacrylate) that is the porous polymer is impregnated with titanium dioxide nanoparticles for blocking UV rays.

The porous polymer of the present invention having a sebum absorption ability may include one or more selected from the group consisting of poly(methyl methacrylate) (PMMA), poly(vinyl pyrrolidone) (PVP), poly(caprolactone) (PCL), and poly(L-lactic acid) (PLLA). Preferably, poly(methyl methacrylate) is used.

The inorganic powder of the present invention may include one or more selected from the group consisting of titanium dioxide ($TiO_2$), zinc oxide, sericite, and iron oxide. Preferably, titanium dioxide is used.

Also, the present invention provides a method for preparing a composite powder formed so that an inorganic powder is uniformly dispersed in a porous polymer to impregnate the porous polymer with the inorganic powder using a spray drying or electro-spraying method, in which the use of an emulsifying agent is avoided, in order to maximize water repellency of the composite powder to promote selective oil absorption for sebum.

More specifically, the cosmetic composition of the present invention may be a makeup cosmetic composition. Conventional makeup cosmetics may be prepared into powders, powder pacts, two-way cakes, powder foundations, liquid foundations, cream foundations, concealers, BB creams, CC creams, makeup bases, primers, eyeshadows, blushers, etc., depending on the component ratio and formulations according to a purpose of use, but the present invention is not limited thereto.

Hereinafter, the present invention will be described in further detail with reference to the accompanying drawings and embodiments thereof. However, it will be apparent to a person having ordinary skill in the art that the present invention is not limited to the following embodiments, and various modifications and changes can be made without departing from the scope of the invention. Unless otherwise defined in this specification, all the technical and scientific terms used herein have the same meanings as what are generally understood by a person skilled in the related art to which the present invention belongs. Therefore, repeated descriptions of the same technical configurations and actions as in the prior art are omitted for clarity.

Figure 1:
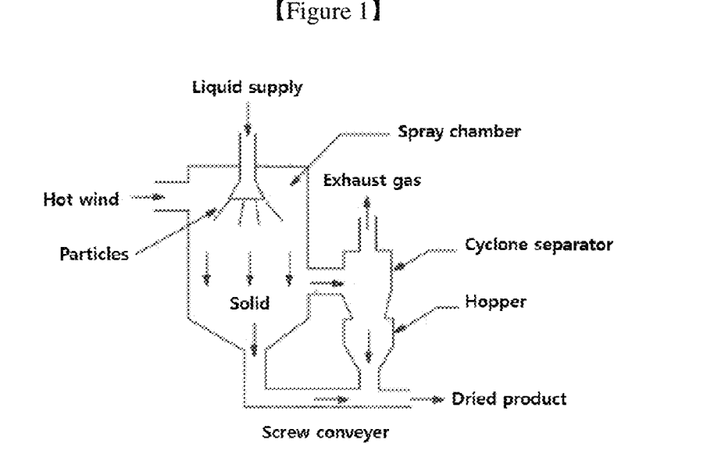
FIG. 1 is a schematic diagram of a spray drying machine used to prepare a composite powder having a porous polymer impregnated with an inorganic powder according to the present invention.

FIG. 1 shows schematic process procedures of a spray drying method using a spray drying machine as a process for preparing a composite powder having a porous polymer impregnated with an inorganic powder according to the present invention. As one exemplary embodiment of the present invention using the spray drying method, a dispersion solution in which a porous polymer having an oil absorption ability for sebum, that is, poly(methyl methacrylate) is mixed with titanium dioxide nanoparticles giving a skin covering power is prepared. Thereafter, the dispersion solution may be added to a spray drying device as shown in FIG. 1 to prepare a composite powder having porous poly(methyl methacrylate) impregnated with titanium dioxide nanoparticles. In this case, the use of an emulsifying agent is preferably avoided to realize super water repellency of the poly(methyl methacrylate) as the porous polymer.

Figure 2:
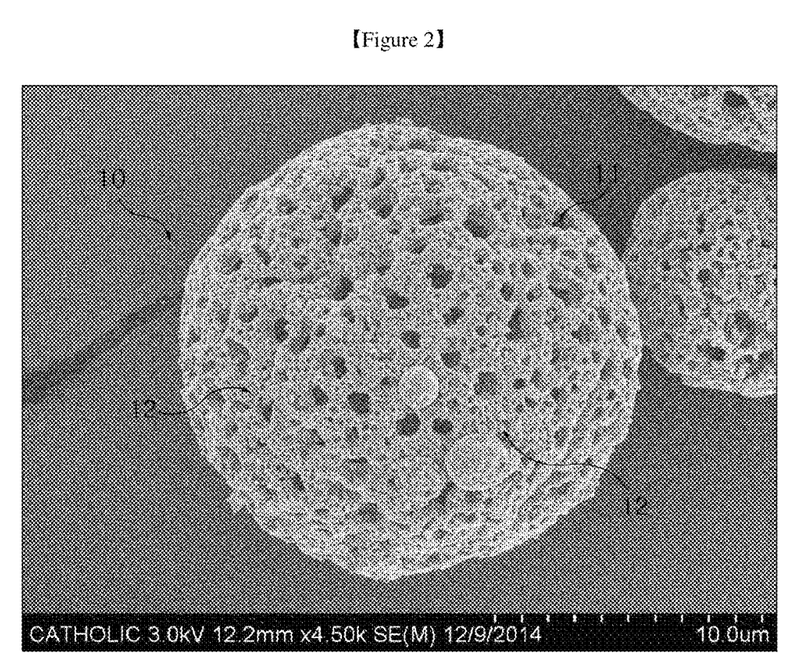
FIG. 2 is a scanning electron microscope (SEM) image of a surface of a composite powder having porous poly(methyl methacrylate) impregnated with titanium dioxide nanoparticles according to the present invention.
Figure 3:
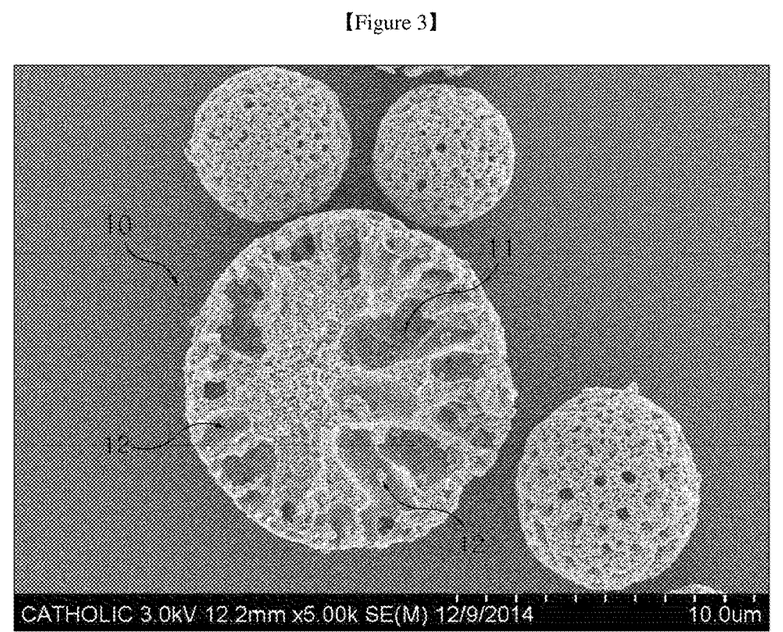
FIG. 3 is an SEM image of a cut-away section of the composite powder having porous poly(methyl methacrylate) impregnated with titanium dioxide nanoparticles according to the present invention.

FIGS. 2 and 3 are SEM images of a surface and cut-away section of the composite powder prepared by the aforementioned spray drying method, that is, a composite powder in which spherical porous poly(methyl methacrylate) is impregnated with 50% by weight of titanium dioxide nanoparticles, based on the total weight of the composite powder. As shown in FIG. 2, it can be seen that pores 11 and hollows 12 are formed on and in a surface of the poly(methyl methacrylate) 10, respectively. As a result, the composite powder of the present invention has pores 11 and hollows 12 formed in a surface thereof in various shapes as well as the surface of the poly(methyl methacrylate) 10, resulting in improved oil absorption rate with respect to the skin.

Figure 4:
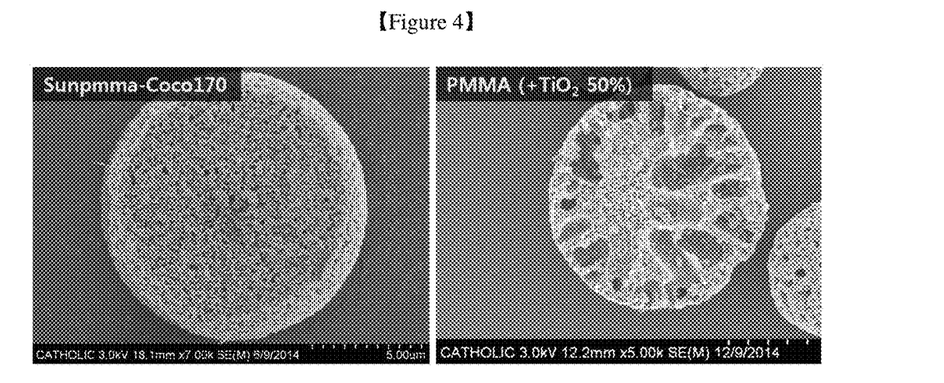
FIG. 4 is an image obtained by quantifying and qualifying an Ti element, which is included in the composite powder having porous poly(methyl methacrylate) impregnated with titanium dioxide nanoparticles according to the present invention, using an energy dispersive X-ray (EDX) analyzer.

FIG. 4 is an image obtained by quantifying and qualifying an Ti element, which is included in the composite powder having porous poly(methyl methacrylate) impregnated with titanium dioxide nanoparticles according to the present invention, using an energy dispersive X-ray (EDX) analyzer. In this case, it can be seen that the titanium dioxide nanoparticles are distributed over the whole poly(methyl methacrylate) in the composite powder of the present invention so that the poly(methyl methacrylate) is uniformly impregnated with the titanium dioxide nanoparticle.

The titanium dioxide nanoparticles are preferably impregnated at a content of 30 to 70% by weight, based on the total weight of the composite powder. When the titanium dioxide nanoparticles are impregnated at a content of less than 30% by weight, the composite powder has a poor effect on skin covering power, On the other hand, when the titanium dioxide nanoparticles are impregnated at a content of greater than 70% by weight, an oil absorption ability may be degraded due to low porosity and a small pore diameter. The content of the titanium dioxide nanoparticles may be used in this range, depending on a purpose thereof. Most preferably, the titanium dioxide nanoparticles are impregnated at a content of 50% by weight, based on the total weight of the composite powder. Accordingly, the composite powder is suitably used for cosmetics in terms of the porosity and pore diameter as well as the skin covering power.

Also, the titanium dioxide nanoparticles preferably have an average particle diameter of 200 to 300 nm as a white pigment for skin care and coverage. When the average particle diameter is less than 200 nm, the covering power is remarkably degraded due to a decrease in degree of visible light scattering. On the other hand, when the average particle diameter is greater than 300 nm, it is difficult to form a composite into the poly(methyl methacrylate). As a result, the titanium dioxide nanoparticles are unsuitable for use as a cosmetic material due to a rough sense of feeling in use.

Figure 5:
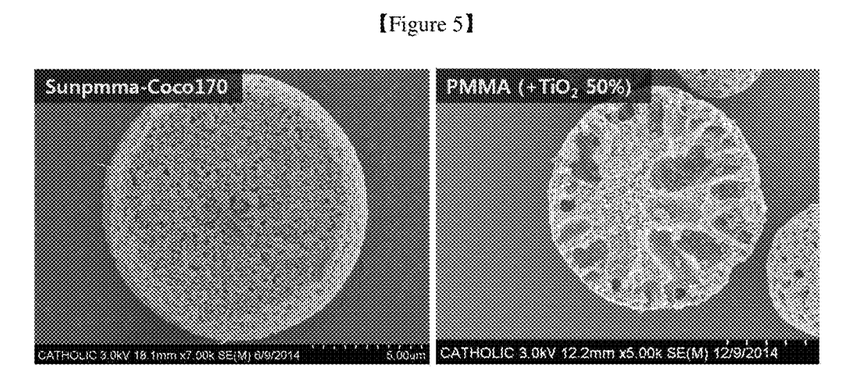
FIG. 5 is an image obtained by comparing a conventional porous poly(methyl methacrylate) powder (PMMA only) and the composite powder (PMMA+$TiO_2$) having porous poly(methyl methacrylate) impregnated with titanium dioxide nanoparticles according to the present invention.

FIG. 5 is an image obtained by comparing a conventional porous poly(methyl methacrylate) powder (PMMA only) and the composite powder (PMMA+$TiO_2$) having porous poly(methyl methacrylate) impregnated with titanium dioxide nanoparticles according to the present invention. As shown, it is revealed that the conventional porous poly(methyl methacrylate) powder (PMMA only, Sunpmma-coco170) has a specific surface area of approximately 70.397 $m^2/g$, an average pore diameter of approximately 23.5 nm, and a porosity of approximately 53.8%, and the porous poly(methyl methacrylate) composite powder (PMMA+$TiO_2$) containing 50% by weight of the titanium dioxide nanoparticles has a specific surface area of approximately 36.134 $m^2/g$, an average pore diameter of approximately 323.7 nm, and a porosity of approximately 69.1%. In particular, the composite powder of the present invention prepared by the spray drying or electro-spraying method may be controlled to have a specific surface area of approximately 10 to 200 $m^2/g$, an average pore diameter of approximately 15 to 500 nm, and a porosity of approximately 50 to 70%, depending on process conditions. The conventional porous poly(methyl methacrylate) powder (PMMA only, Sunpmma-coco170) has a relatively larger specific surface area but a smaller average pore diameter and porosity due to a single-sized mesoporous structure, but the composite powder (PMMA+$TiO_2$) of the present invention is much more advantageous in absorbing oils through a capillary action because pore channels are formed due to a multi-porous (Micro+Meso+Macro) structure.

Figure 6:
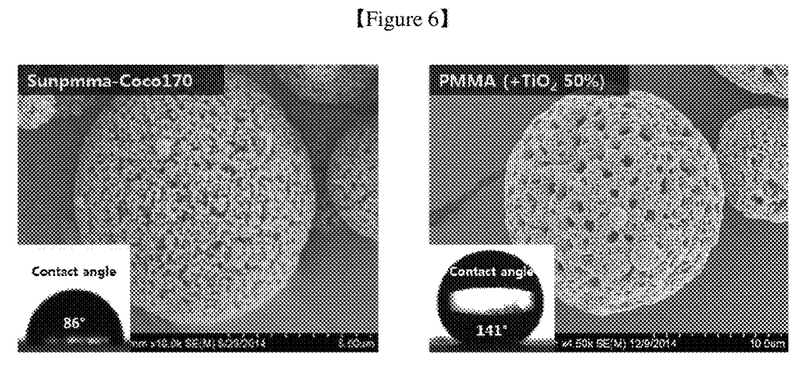
FIG. 6 is an image obtained by comparing contact angles of the conventional porous poly(methyl methacrylate) powder (PMMA only) and the composite powder (PMMA+$TiO_2$) having porous poly(methyl methacrylate) impregnated with titanium dioxide nanoparticles according to the present invention with respect to moisture.

FIG. 6 is an image obtained by comparing contact angles of the conventional porous poly(methyl methacrylate) powder (PMMA only, Sunpmma-coco170, Sunjin Chemical Co., Ltd.) and the composite powder (PMMA+$TiO_2$) having porous poly(methyl methacrylate) impregnated with titanium dioxide nanoparticles according to the present invention with respect to moisture. Here, it is revealed that the composite powder of the present invention has superior water repellency, compared to the conventional porous poly (methyl methacrylate) (PMMA only, Sunpmma-coco170, Sunjin Chemical Co., Ltd.). Such water repellency allows the skin to repel moisture and selectively absorb only sebum when makeups are applied to the skin.

The water repellency of the composite powder (PMMA+ $TiO_2$) having porous poly(methyl methacrylate) impregnated with the titanium dioxide nanoparticles according to the present invention is a property obtained by avoiding the use of an emulsifying agent serving to reduce the water repellency during a manufacturing process. For this purpose, the composite powder (PMMA+$TiO_2$) of the present invention is preferably prepared using a spray drying or electro-spraying method. Because the conventional porous poly (methyl methacrylate) (PMMA, Sunpmma-coco170, Sunjin Chemical Co., Ltd.) is produced by means of emulsion polymerization, the use of an emulsifying agent is inevitable, and it is impossible to completely remove the emulsifying agent, resulting in degraded water repellency of the powder. Therefore, the water repellency may be maximized in the present invention by preparing the composite powder using a spray drying or electro-spraying method as a method for selective oil absorption of sebum in order to avoid the use of the emulsifying agent serving to impede the water repellency of the powder. This may be checked using a moisture contact angle test shown in FIG. 6.

Figure 7:
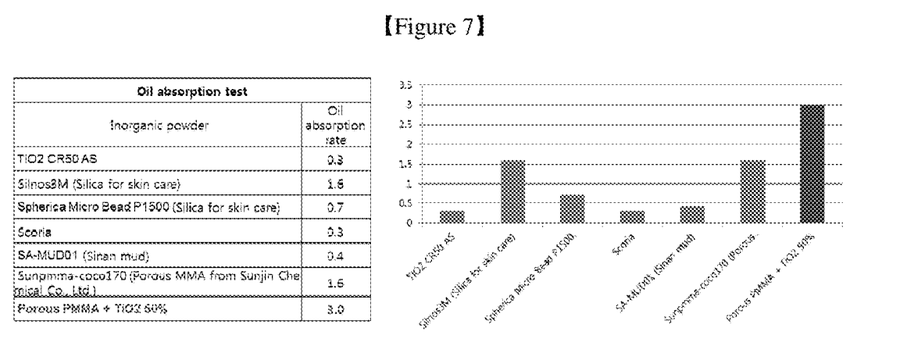
FIG. 7 shows results of measuring an oil absorption rate of the composite powder having porous poly(methyl methacrylate) impregnated with titanium dioxide nanoparticles according to the present invention.

FIG. 7 shows results of testing an oil absorption rate of the composite powder (PMMA+$TiO_2$) having porous poly(methyl methacrylate) impregnated with titanium dioxide nanoparticles according to the present invention. As shown, it is revealed that the oil absorption rate of the composite powder (PMMA+$TiO_2$) increases 10 times higher than that of the conventional inorganic powder ($TiO_2$ CR50 AS). Also, it is revealed that the oil absorption rate of the composite powder (PMMA+$TiO_2$) increases twice higher than that of the conventional porous poly(methyl methacrylate) (PMMA only). This effect is obtained by maintaining the pore diameter and porosity of the composite powder of the present invention higher than the conventional porous poly(methyl methacrylate) even when the composite powder contains 50% by weight of titanium dioxide.

In addition to the composite powder having the porous polymer impregnated with the inorganic powder, the cosmetic composition of the present invention may further include a functional additive and components included in the conventional cosmetic compositions. The functional additive may include components selected from the group consisting of water-soluble vitamins, oil-soluble vitamins, polymeric peptides, polymeric polysaccharides, sphingolipids, and seaweed extracts. Also, the components included in the conventional cosmetic composition may be mixed together with the functional additive, when necessary. Components to be further blended in the cosmetic composition may include an oily component, a moisturizing agent, an emollient, a surfactant, organic and inorganic pigments, an organic powder, a UV absorbent, a preservative, a bactericide, an antioxidant, a plant extract, a pH regulator, an alcohol, a color, a fragrance, a blood flow stimulant, a cooling agent, a control agent, purified water, etc.

The present invention will be described with reference to the accompanying drawings, but it is merely one example of various embodiments including the gist of the present invention, and an object thereof is to allow a person having ordinary skill in the art to easily embody the present invention, and thus it is apparent that the present invention is not limited to only the embodiments as described above. Therefore, the protection scope of the present invention should be interpreted by the following claims, and all the technical spirits falling within the equivalent scope by modifications, replacements, and substitutions made within a range which does not deviate from the gist of the present invention should be included in the scope of the present invention. Also, it is apparent that some configurations of the drawings are provided to clearly describe the configurations.

MODE FOR INVENTION

Hereinafter, preparative examples for embodying the composite powder having a porous polymer impregnated with an inorganic powder according to the present invention will be described in detail. However, it will be apparent to a person having ordinary skill in the art that the present invention is not limited to the preparative examples, and other applications and modifications are also made to the preparative examples of the present invention.

PREPARATIVE EXAMPLES

The following components are prepared to prepare a poly(methyl methacrylate) composite powder (PMMA+ $TiO_2$) impregnated with titanium dioxide according to the present invention.

Titanium dioxide ($TiO_2$: OTS-2 $TiO_2$ CR-50 commercially available from Daito Kase)

Poly(methyl methacrylate) (PMMA: IH830B commercially available from LG PMMA)

Dichloromethane anhydrous (DCM commercially available from Sigma-Aldrich; Purity>99.8%)

Hexanol (orl-hexanol commercially available from Sigma-Aldrich; Purity>99%)

1. Spray Drying 1) 40 g of PMMA is dissolved in 1 L of a solvent (DCM:hexanol=9:1 (% by weight)).

2) 40 g of $TiO_2$ is added to the PMMA solution, and then dispersed using a homogenizer.

3) The PMMA solution in which $TiO_2$ is dispersed is spray-dried.

4) The humidity in a spray drying machine is maintained to be 30% or more, and the temperature in the spray drying machine is maintained at room temperature.

5) The PMMA solution is spray-dried under conditions of a feed rate of 20%, an aspirator capacity of 70%, and a pressure of 20 atm. The PMMA solution in which $TiO_2$ is dispersed is continuously stirred during spray drying using a stirring machine.

6) The spray-dried $TiO_2$/PMMA composite powder particles are thoroughly washed, and then freeze-dried to completely remove the residual solvent, thereby obtaining the $TiO_2$/PMMA composite powder.

2. Electro-spraying 1) 0.4 g of PMMA is dissolved in 10 mL of a solvent (DCM:hexanol=9:1 (% by weight)).

2) 0.4 g of $TiO_2$ is added to the PMMA solution, and then dispersed using a sonicator.

3) The PMMA solution in which $TiO_2$ is dispersed is electro-sprayed.

4) The humidity in an electro-spraying cage is maintained to be 30% or more, and the temperature in the electro-spraying cage is maintained at room temperature.

5) The PMMA solution is electro-sprayed under conditions of a feed rate of 0.01 mL/min, a voltage of 10 kV, and a distance of 15 cm.

6) The electro-sprayed TiO$_2$/PMMA composite powder particles are thoroughly washed, and then freeze-dried to completely remove the residual solvent, thereby obtaining the TiO$_2$/PMMA composite powder.

INDUSTRIAL APPLICABILITY

The cosmetic composition of the present invention, which includes the composite powder having a porous polymer impregnated with an inorganic powder, can be formulated into makeup cosmetic materials such as powders, powder pacts, two-way cakes, powder foundations, liquid foundations, cream foundations, concealers, BB creams, CC creams, makeup bases, primers, eyeshadows, blushers, etc. In this case, the formulations can be properly chosen and altered according to a purpose, but the present invention is not particularly limited thereto.

The invention claimed is:

1. A composite powder for skin cover pigment having a porous polymer impregnated with an inorganic powder,
   wherein the porous polymer comprises one or more selected from the group consisting of poly(methyl methacrylate) (PMMA), poly(vinyl pyrrolidone) (PVP), poly(caprolactone) (PCL), and poly(L-lactic acid) (PLLA), and
   the inorganic powder comprises titanium dioxide (TiO$_2$),
   wherein the composite powder has a porosity of 50 to 70%,
   wherein the titanium dioxide has an average particle diameter of 200 to 300 nm,
   wherein the titanium dioxide is impregnated at a content of 30 to 70% by weight based on the total weight of the composite powder, and
   wherein the porous polymer has an average pore diameter of 15 to 500 nm.

2. The composite powder for skin cover pigment of claim 1, wherein the composite powder has porous poly(methyl methacrylate) impregnated with titanium dioxide nanoparticles.

3. The composite powder for skin cover pigment of claim 1, wherein the titanium dioxide is impregnated at a content of 50% by weight, based on the total weight of the composite powder.

4. The composite powder for skin cover pigment of claim 2, wherein the porous poly(methyl methacrylate) has a specific surface area of 10 to 200 m$^2$/g.

5. A cosmetic composition comprising the composite powder according to claim 1.

6. A method for preparing a composite powder having a porous polymer impregnated with an inorganic powder according to claim 1,
   wherein the composite powder is prepared by dispersing the inorganic powder in a porous polymer solution and spray-drying or electro-spraying the dispersed porous polymer solution.

* * * * *